(12) United States Patent
Berzak et al.

(10) Patent No.: US 8,080,005 B1
(45) Date of Patent: Dec. 20, 2011

(54) CLOSED LOOP CRYOSURGICAL PRESSURE AND FLOW REGULATED SYSTEM

(75) Inventors: Nir Berzak, Givataim (IL); Simon Sharon, Ma'ayan Zvi (IL); Nadav Lavochkin, Hadera (IL)

(73) Assignee: IceCure Medical Ltd., Caesarea (IL)

( * ) Notice: Subject to any disclaimer, the term of this patent is extended or adjusted under 35 U.S.C. 154(b) by 0 days.

(21) Appl. No.: 12/846,047

(22) Filed: Jul. 29, 2010

Related U.S. Application Data

(60) Provisional application No. 61/353,375, filed on Jun. 10, 2010.

(51) Int. Cl.
*A61B 18/02* (2006.01)
(52) U.S. Cl. .......................................... 606/22; 606/24
(58) Field of Classification Search ................ 606/23–25
See application file for complete search history.

(56) References Cited

U.S. PATENT DOCUMENTS

| | | | |
|---|---|---|---|
| 3,234,746 A | 2/1966 | Smith |
| 3,358,472 A | 12/1967 | Kipling |
| 3,664,344 A | 5/1972 | Bryne |
| 3,699,775 A | 10/1972 | Cowans |
| 3,712,306 A | 1/1973 | Bryne |
| 3,736,936 A | 6/1973 | Basiulis |
| 3,800,552 A | 4/1974 | Sollami |
| 3,862,630 A | 1/1975 | Balamuth |
| 3,882,849 A | 5/1975 | Jamshidi |
| 3,938,505 A | 2/1976 | Jamshidi |
| 3,971,383 A | 7/1976 | Van Gerven |
| 4,082,096 A | 4/1978 | Benson |
| 4,091,634 A | 5/1978 | Shepherd |
| 4,127,903 A | 12/1978 | Schachar |
| 4,200,104 A | 4/1980 | Harris |
| 4,211,231 A | 7/1980 | Rzasa |
| 4,279,626 A | 7/1981 | Buchmuller |
| 4,306,568 A | 12/1981 | Torre |
| 4,313,306 A | 2/1982 | Torre |

(Continued)

FOREIGN PATENT DOCUMENTS

CA 2437079 6/2004

(Continued)

OTHER PUBLICATIONS

U.S. Appl. No. 12/360,221, filed Jan. 27, 2009, Levin, Arbel Medical Ltd.

(Continued)

*Primary Examiner* — Michael Peffley
*Assistant Examiner* — Thomas Giuliani
(74) *Attorney, Agent, or Firm* — The Law Office of Michael E. Kondoudis

(57) ABSTRACT

A system for selectively cooling and warming a cryosurgical instrument using a dual phase cryogen, including: two sources of the cryogen, a first source storing liquid phase cryogen and having a first source heater therein that selectively converts at least some of the liquid phase cryogen into gaseous phase cryogen and a second source storing the gaseous phase cryogen; a cryogen delivery control section selectively delivering cryogen to the tip; a cryogen return path from the tip to the first and second sources; a cryogen return control section that includes a pump that pumps the returning cryogen to the second source; and a pressure control section including a first pressure sensor that senses a pressure in the first source, a second pressure sensor that senses a pressure in the second source, and a pressure regulator that regulates the pressure of the first source based on information from the pressure sensors.

8 Claims, 4 Drawing Sheets

U.S. PATENT DOCUMENTS

| | | | |
|---|---|---|---|
| 4,367,744 A | 1/1983 | Sole | |
| 4,428,748 A | 1/1984 | Peyman | |
| 4,463,458 A | 8/1984 | Seidner | |
| 4,481,948 A | 11/1984 | Sole | |
| 4,487,253 A | 12/1984 | Malek | |
| 4,552,208 A | 11/1985 | Sorensen | |
| 4,570,626 A | 2/1986 | Norris | |
| 4,573,525 A | 3/1986 | Boyd | |
| 4,611,654 A | 9/1986 | Buchsel | |
| 4,617,018 A | 10/1986 | Nishi | |
| 4,676,225 A | 6/1987 | Bartera | |
| 4,726,194 A | 2/1988 | Mackay | |
| 4,765,396 A | 8/1988 | Seidenberg | |
| 4,770,171 A | 9/1988 | Sweren | |
| 4,802,475 A | 2/1989 | Weshahy | |
| 4,831,856 A | 5/1989 | Gano | |
| 4,946,460 A | 8/1990 | Merry | |
| 5,026,387 A | 6/1991 | Thomas | |
| 5,047,043 A | 9/1991 | Kubota | |
| 5,108,390 A | 4/1992 | Potocky | |
| 5,147,355 A | 9/1992 | Friedman | |
| 5,188,102 A | 2/1993 | Idemoto | |
| 5,214,925 A | 6/1993 | Hoy | |
| 5,222,937 A | 6/1993 | Kagawa | |
| 5,224,943 A | 7/1993 | Goddard | |
| 5,243,826 A | 9/1993 | Longsworth | |
| 5,254,082 A | 10/1993 | Takase | |
| 5,254,116 A | 10/1993 | Baust | |
| 5,261,923 A | 11/1993 | Soares | |
| 5,263,957 A | 11/1993 | Davison | |
| 5,264,116 A | 11/1993 | Apelian | |
| 5,275,595 A | 1/1994 | Dobak | |
| 5,281,215 A | 1/1994 | Milder | |
| 5,295,484 A | 3/1994 | Marcus | |
| 5,324,286 A | 6/1994 | Fowle | |
| 5,330,745 A | 7/1994 | Mcdow | |
| 5,334,181 A | 8/1994 | Rubinsky | |
| 5,342,380 A | 8/1994 | Hood | |
| 5,361,591 A | 11/1994 | Caldwell | |
| 5,391,144 A | 2/1995 | Sakurai | |
| 5,411,374 A | 5/1995 | Gram | |
| 5,417,073 A | 5/1995 | James | |
| 5,423,807 A | 6/1995 | Milder | |
| 5,429,138 A | 7/1995 | Jamshidi | |
| 5,438,837 A | 8/1995 | Caldwell | |
| 5,441,512 A | 8/1995 | Muller | |
| 5,445,462 A | 8/1995 | Johnson | |
| 5,452,582 A | 9/1995 | Longsworth | |
| 5,488,831 A | 2/1996 | Griswold | |
| 5,516,505 A | 5/1996 | Mcdow | |
| 5,520,682 A | 5/1996 | Baust | |
| 5,526,821 A | 6/1996 | Jamshidi | |
| 5,547,473 A | 8/1996 | Peyman | |
| 5,573,532 A | 11/1996 | Chang | |
| 5,600,143 A | 2/1997 | Roberts | |
| 5,603,221 A * | 2/1997 | Maytal | 62/51.2 |
| 5,632,743 A * | 5/1997 | Clarke | 606/24 |
| 5,647,868 A | 7/1997 | Chinn | |
| 5,654,279 A | 8/1997 | Rubinsky | |
| 5,658,276 A | 8/1997 | Griswold | |
| 5,674,218 A * | 10/1997 | Rubinsky et al. | 606/20 |
| 5,683,592 A | 11/1997 | Bartholomew | |
| 5,687,776 A | 11/1997 | Forgash | |
| 5,716,353 A | 2/1998 | Matsuura | |
| 5,720,743 A | 2/1998 | Bischof | |
| 5,728,130 A | 3/1998 | Ishikawa | |
| 5,735,845 A | 4/1998 | Zupkas | |
| 5,771,946 A | 6/1998 | Kooy | |
| 5,787,940 A | 8/1998 | Bonn | |
| 5,800,448 A | 9/1998 | Banko | |
| 5,800,487 A | 9/1998 | Mikus | |
| 5,814,040 A | 9/1998 | Nelson | |
| 5,860,971 A * | 1/1999 | Clarke | 606/24 |
| 5,868,673 A | 2/1999 | Vesely | |
| 5,885,276 A | 3/1999 | Ammar | |
| 5,899,897 A | 5/1999 | Rabin | |
| 5,906,612 A | 5/1999 | Chinn | |
| 5,906,628 A | 5/1999 | Miyawaki | |
| 5,910,104 A | 6/1999 | Dobak | |
| 5,921,982 A | 7/1999 | Lesh | |
| 5,976,092 A | 11/1999 | Chinn | |
| 5,976,505 A | 11/1999 | Henderson | |
| 5,992,158 A | 11/1999 | Goddard | |
| 6,012,453 A | 1/2000 | Tsais | |
| 6,024,750 A | 2/2000 | Mastri | |
| 6,027,499 A | 2/2000 | Johnston | |
| 6,032,068 A | 2/2000 | Daniel | |
| 6,032,675 A | 3/2000 | Rubinsky | |
| 6,035,657 A | 3/2000 | Dobak | |
| 6,036,667 A | 3/2000 | Manna | |
| 6,039,730 A | 3/2000 | Rabin | |
| 6,041,787 A | 3/2000 | Rubinsky | |
| 6,042,342 A | 3/2000 | Orian | |
| 6,053,906 A | 4/2000 | Honda | |
| 6,059,820 A | 5/2000 | Baronov | |
| 6,063,098 A | 5/2000 | Houser | |
| 6,095,149 A | 8/2000 | Sharkey | |
| 6,142,991 A | 11/2000 | Schatzberger | |
| 6,152,894 A | 11/2000 | Kubler | |
| 6,182,666 B1 | 2/2001 | Dobak | |
| 6,200,308 B1 | 3/2001 | Pope | |
| 6,206,832 B1 | 3/2001 | Downey | |
| 6,212,904 B1 | 4/2001 | Arkharov | |
| 6,216,029 B1 | 4/2001 | Paltieli | |
| 6,235,018 B1 | 5/2001 | LePivert | |
| 6,237,355 B1 | 5/2001 | Li | |
| 6,251,105 B1 | 6/2001 | Mikus | |
| 6,270,494 B1 | 8/2001 | Kovalcheck | |
| 6,280,407 B1 | 8/2001 | Manna | |
| 6,354,088 B1 | 3/2002 | Emmer | |
| 6,355,033 B1 | 3/2002 | Moorman | |
| 6,358,264 B2 | 3/2002 | Banko | |
| 6,379,348 B1 | 4/2002 | Onik | |
| 6,383,180 B1 | 5/2002 | Lalonde | |
| 6,383,181 B1 | 5/2002 | Johnston | |
| 6,411,852 B1 | 6/2002 | Danek | |
| 6,413,263 B1 | 7/2002 | Lobdill | |
| 6,423,009 B1 | 7/2002 | Downey | |
| 6,432,102 B2 | 8/2002 | Joye | |
| 6,457,212 B1 | 10/2002 | Craig | |
| 6,468,268 B1 | 10/2002 | Abboud | |
| 6,468,269 B1 | 10/2002 | Korpan | |
| 6,471,217 B1 | 10/2002 | Hayfield | |
| 6,482,178 B1 | 11/2002 | Andrews | |
| 6,497,714 B1 | 12/2002 | Ishikawa | |
| 6,500,109 B2 | 12/2002 | Tokita | |
| 6,503,246 B1 | 1/2003 | Har-Shai | |
| 6,508,814 B2 | 1/2003 | Tortal | |
| 6,513,336 B2 | 2/2003 | Zurecki | |
| 6,547,784 B1 | 4/2003 | Thompson | |
| 6,551,309 B1 | 4/2003 | LePivert | |
| 6,562,030 B1 | 5/2003 | Abboud | |
| 6,565,556 B1 | 5/2003 | Korpan | |
| 6,581,390 B2 | 6/2003 | Emmer | |
| 6,582,426 B2 | 6/2003 | Moorman | |
| 6,631,615 B2 | 10/2003 | Drube | |
| 6,640,556 B2 | 11/2003 | Ursan | |
| 6,659,730 B2 | 12/2003 | Gram | |
| 6,659,956 B2 | 12/2003 | Barzell | |
| 6,672,095 B1 | 1/2004 | Luo | |
| 6,678,621 B2 | 1/2004 | Wiener | |
| 6,682,525 B2 * | 1/2004 | Lalonde et al. | 606/22 |
| 6,698,423 B1 | 3/2004 | Honkonen | |
| 6,702,761 B1 | 3/2004 | Damadian | |
| 6,761,715 B2 | 7/2004 | Carroll | |
| 6,765,333 B1 | 7/2004 | Mariaucue | |
| 6,768,917 B1 | 7/2004 | Van Vaals | |
| 6,772,766 B2 | 8/2004 | Gallo | |
| 6,786,902 B1 | 9/2004 | Rabin | |
| 6,824,543 B2 | 11/2004 | Lentz | |
| 6,852,706 B1 | 2/2005 | Heber-Katz | |
| 6,858,025 B2 | 2/2005 | Maurice | |
| 6,869,439 B2 | 3/2005 | White | |
| 6,889,695 B2 | 5/2005 | Pankratov | |
| 6,898,940 B2 | 5/2005 | Gram | |
| 6,908,472 B2 | 6/2005 | Wiener | |
| 6,910,510 B2 | 6/2005 | Gale | |

| Patent No. | Date | Name |
|---|---|---|
| 6,913,604 B2 | 7/2005 | Mihalik |
| 6,932,771 B2 | 8/2005 | Whitmore |
| 6,936,045 B2 | 8/2005 | Yu |
| 6,942,659 B2 | 9/2005 | Lehmann |
| 6,951,569 B2 | 10/2005 | Nohilly |
| 6,954,977 B2 | 10/2005 | Maguire |
| 6,995,493 B2 | 2/2006 | Isoda |
| 7,001,378 B2 | 2/2006 | Yon |
| 7,025,762 B2 | 4/2006 | Johnston |
| 7,025,767 B2 | 4/2006 | Schaefer |
| 7,071,690 B2 | 7/2006 | Butts |
| 7,081,111 B2 | 7/2006 | Svaasand |
| 7,101,367 B2 | 9/2006 | Xiao |
| 7,128,739 B2 | 10/2006 | Prakash |
| 7,137,978 B2 * | 11/2006 | Levin ............................ 606/22 |
| 7,144,228 B2 | 12/2006 | Emmer |
| 7,151,374 B2 | 12/2006 | Doty |
| 7,160,291 B2 | 1/2007 | Damasco |
| 7,160,292 B2 | 1/2007 | Moorman |
| 7,165,422 B2 | 1/2007 | Little |
| 7,189,228 B2 | 3/2007 | Eum |
| 7,207,985 B2 | 4/2007 | Duong |
| 7,213,400 B2 | 5/2007 | Dickerson |
| 7,223,080 B2 | 5/2007 | Duron |
| 7,250,046 B1 | 7/2007 | Fallat |
| 7,252,648 B2 | 8/2007 | Honda |
| 7,255,693 B1 | 8/2007 | Johnston |
| 7,273,479 B2 | 9/2007 | Littrup |
| 7,278,991 B2 | 10/2007 | Morris |
| 7,280,623 B2 | 10/2007 | Gupta |
| 7,282,919 B2 | 10/2007 | Doty |
| 7,288,089 B2 | 10/2007 | Yon |
| 7,318,327 B2 | 1/2008 | Dickerson |
| 7,344,530 B2 | 3/2008 | Bischoff |
| 7,344,531 B2 | 3/2008 | Bischoff |
| 7,354,434 B2 | 4/2008 | Zvuloni |
| 7,361,187 B2 | 4/2008 | Duong |
| 7,381,207 B2 | 6/2008 | Duong |
| 7,407,501 B2 * | 8/2008 | Zvuloni ............................ 606/20 |
| 7,425,211 B2 | 9/2008 | Levin et al. |
| 7,458,968 B2 | 12/2008 | Carroll |
| 7,481,806 B2 | 1/2009 | Levin |
| 7,485,117 B2 | 2/2009 | Damasco |
| 7,498,812 B2 | 3/2009 | Doty |
| 7,510,554 B2 | 3/2009 | Duong |
| 7,563,260 B2 | 7/2009 | Whitmore |
| 7,731,711 B2 | 6/2010 | Levin |
| 7,803,154 B2 | 9/2010 | Toubia et al. |
| 2001/0047129 A1 | 11/2001 | Hall |
| 2002/0016540 A1 | 2/2002 | Mikus |
| 2002/0022832 A1 | 2/2002 | Mikus |
| 2002/0040220 A1 | 4/2002 | Zvuloni |
| 2002/0077654 A1 | 6/2002 | Javier |
| 2002/0085921 A1 | 7/2002 | Gram |
| 2002/0144509 A1 | 10/2002 | Chalk |
| 2002/0156469 A1 | 10/2002 | Yon |
| 2002/0157402 A1 | 10/2002 | Drube |
| 2002/0160640 A1 | 10/2002 | Korpan |
| 2002/0161385 A1 | 10/2002 | Wiener |
| 2003/0060762 A1 | 3/2003 | Zvuloni |
| 2003/0079480 A1 | 5/2003 | Emmer |
| 2003/0126867 A1 | 7/2003 | Drube |
| 2003/0135119 A1 | 7/2003 | Lee |
| 2003/0181897 A1 | 9/2003 | Thomas |
| 2003/0220635 A1 | 11/2003 | Knowlton |
| 2004/0024391 A1 | 2/2004 | Cytron |
| 2004/0055316 A1 | 3/2004 | Emmer |
| 2004/0078033 A1 | 4/2004 | Levin |
| 2004/0215178 A1 | 10/2004 | Maurice |
| 2005/0016185 A1 | 1/2005 | Emmer |
| 2005/0038422 A1 | 2/2005 | Maurice |
| 2005/0056027 A1 | 3/2005 | White |
| 2005/0086949 A1 | 4/2005 | Noble |
| 2005/0106153 A1 | 5/2005 | Nordouist |
| 2005/0177147 A1 | 8/2005 | Vancelette |
| 2005/0192564 A1 | 9/2005 | Cosman |
| 2005/0214268 A1 | 9/2005 | Cavanagh |
| 2005/0274142 A1 | 12/2005 | Corey |
| 2006/0049274 A1 | 3/2006 | Hume |
| 2006/0053165 A1 | 3/2006 | Hume |
| 2006/0079867 A1 | 4/2006 | Berzak |
| 2006/0122590 A1 | 6/2006 | Bliweis |
| 2006/0155267 A1 | 7/2006 | Berzak |
| 2006/0155268 A1 | 7/2006 | Amir |
| 2006/0264920 A1 | 11/2006 | Duong |
| 2006/0293647 A1 | 12/2006 | McRae |
| 2007/0000259 A1 | 1/2007 | Brook |
| 2007/0093710 A1 | 4/2007 | Maschke |
| 2007/0129626 A1 | 6/2007 | Mahesh |
| 2007/0129629 A1 | 6/2007 | Beauregard |
| 2007/0149959 A1 | 6/2007 | DeLonzor |
| 2007/0166171 A1 | 7/2007 | Kondo |
| 2007/0167939 A1 | 7/2007 | Duong |
| 2007/0276360 A1 | 11/2007 | Johnston |
| 2008/0027419 A1 | 1/2008 | Hamel |
| 2008/0051774 A1 | 2/2008 | Ofir |
| 2008/0051776 A1 | 2/2008 | Bliweis |
| 2008/0115509 A1 | 5/2008 | Gullickson |
| 2008/0119834 A1 | 5/2008 | Vancelette |
| 2008/0119838 A1 | 5/2008 | Vancelette |
| 2008/0319433 A1 | 12/2008 | Geiselhart |
| 2009/0011032 A1 | 1/2009 | LePivert |

FOREIGN PATENT DOCUMENTS

| | | |
|---|---|---|
| DE | 202004008875 U1 | 8/2004 |
| DE | 102005050344 | 5/2007 |
| EP | 0292922 B1 | 11/1988 |
| EP | 395307 A2 | 10/1990 |
| EP | 570301 | 11/1993 |
| EP | 955012 | 11/1999 |
| EP | 919197 B1 | 2/2005 |
| GB | 1108905 | 4/1968 |
| GB | 1402737 | 8/1975 |
| GB | 1473856 | 5/1977 |
| GB | 1534472 | 12/1978 |
| GB | 2336781 | 11/1999 |
| GB | 2409815 A1 | 7/2005 |
| JP | 2004041428 A2 | 2/2004 |
| JP | 2007144180 A2 | 6/2007 |
| JP | 2007167100 | 7/2007 |
| WO | WO8303961 A1 | 11/1983 |
| WO | WO9637158 A1 | 11/1996 |
| WO | WO9639960 A1 | 12/1996 |
| WO | WO9947876 A1 | 9/1999 |
| WO | WO0137919 A2 | 5/2001 |
| WO | WO0141683 A2 | 6/2001 |
| WO | WO0197702 | 12/2001 |
| WO | WO0202026 A1 | 1/2002 |
| WO | WO03015651 A1 | 2/2003 |
| WO | WO2004051409 A2 | 8/2004 |
| WO | WO0189183 A1 | 10/2004 |
| WO | WO2004060465 | 2/2005 |
| WO | WO2004093635 A2 | 6/2005 |
| WO | WO2005098308 A1 | 10/2005 |
| WO | WO2005000106 A2 | 12/2005 |
| WO | WO2006116457 A2 | 11/2006 |
| WO | WO2006127467 | 11/2006 |
| WO | WO2007028232 A1 | 3/2007 |
| WO | WO2007086056 A2 | 8/2007 |
| WO | WO2007129308 | 11/2007 |

OTHER PUBLICATIONS

U.S. Appl. No. 11/851,055, filed Sep. 6, 2007, Toubia et al., Arbel Medical Ltd.
U.S. Appl. No. 12/017,035, filed Jan. 20, 2008, Toubia et al., Arbel Medical Ltd.
U.S. Appl. No. 11/763,093, filed Jun. 14, 2007, Levin et al., Arbel Medical Ltd.
U.S. Appl. No. 12/278,733, filed Nov. 5, 2008, Levin et al., Arbel Medical Ltd.
U.S. Appl. No. 11/857,085, filed Sep. 18, 2007, Levin et al., Arbel Medical Ltd.
U.S. Appl. No. 12/668,428, filed Sep. 7, 2010, Levin et al.
U.S. Appl. No. 12/673,506, filed Feb. 15, 2010, Levin et al.
U.S. Appl. No. 12/237,805, filed Sep. 25, 2008, Levin et al., Arbel Medical Ltd.

U.S. Appl. No. 12/313,611, filed Nov. 21, 2008, Toubia et al., Arbel Medical Ltd.
U.S. Appl. No. 12/812,819, filed Sep. 29, 2010, Toubia et al., IceCure Medical Ltd.
U.S. Appl. No. 12/988,233, filed Oct. 15, 2010, Toubia et al., Arbel Medical Ltd.
U.S. Appl. No. 12/611,938, filed Nov. 4, 2009, Levin.
U.S. Appl. No. 12/731,219, filed Mar. 25, 2010, Berzak et al., IceCure Medical Ltd.
U.S. Appl. No. 12/700,761, filed Feb. 5, 2010, Levin.
U.S. Appl. No. 12/778,172, filed May 12, 2010, Berzak et al., IceCure Medical Ltd.
Verkin et al., Low Temperatures in Stomatology, Naukova Dumka, 1990, pp. 62-63, Kiev.
International Search Report and Written Opinion dated Nov. 5, 2008 in corresponding International Application No. PCT/IL2008/000794.
Qi et al., Development and performance test of a cryoprobe with heat transfer configuration enhancement, Cryogenics, 2006, pp. 881-887, vol. 46, Elsevier.
International Search Report dated Mar. 25, 2010 in corresponding International Application No. PCT/IB2009/052615.
International Search Report and Written Opinion dated Jul. 23, 2009 in corresponding International Application No. PCT/IL2009/000062.
International Search Report and Written Opinion dated Dec. 22, 2008 in corresponding International Application No. PCT/IL2008/001114.
International Search Report and Written Opinion dated Sep. 4, 2009 in corresponding International Application No. PCT/IB2009/051532.
Office Action dated Jan. 22, 2010 in Application No. EP 07805563.9.
International Search Report and Written Opinion dated Nov. 28, 2008 in corresponding International Application No. PCT/IL2008/000943.
International Search Report and Written Opinion dated Jan. 29, 2008 in corresponding International Application No. PCT/IL2007/001103.
International Search Report and Written Opinion dated Jan. 30, 2008 in corresponding International Application No. PCT/IL2007/001142.
International Search Report and Written Opinion dated Nov. 6, 2007 in corresponding International Application No. PCT/IL2007/000974.
Qi et al., Flow boiling of liquid nitrogen in micro-tubes: Part I—onset of nucleate boiling, two phase flow instability and two phase flow drop, International Journal of Heat and Mass Transfer, 2007, pp. 4999-5016, vol. 50, Elsevier.
Qi et al., Flow boiling of liquid nitrogen in micro-tubes: Part II—heat transfer characteristics and critical heat flux, International Journal of Heat and Mass Transfer, 2007, pp. 5017-5030, vol. 50, Elsevier.
Zhang et al., Two phase flow characteristics of liquid nitrogen in vertically upward 0.5 and 1.0 mm micro-tubes: Visualization studies, Cryogenics, 2009, pp. 565-575, vol. 49, Elsevier.
International Search Report and Written Opinion dated Aug. 24, 2010 in corresponding International Application PCT/US2010/34467.

* cited by examiner

CLOSED LOOP CRYOSURGICAL PRESSURE AND FLOW REGULATED SYSTEM

CROSS-REFERENCE TO RELATED APPLICATION

This application claims the benefit of U.S. provisional patent application No. 61/353,375, filed Jun. 10, 2010, the disclosure of which is incorporated by reference.

BACKGROUND

1. Technical Field

Embodiments of the present invention relate to cryogen flow regulation systems and, more particularly, to devices and systems for regulating pressure in a closed loop in which pressure is at least partially regulated through regulating flow through the system.

2. Description of Background Art

Various cryosurgical systems that regulate cryogen pressure are known. Further, various approached to cryogen pressure regulation are known. Examples include U.S. Patent Publication Nos. 2009/0270851 and 2007/0149957 and the following U.S. Pat. Nos. 5,520,682, 7,192,426, and 5,334,181. Known systems and approaches, however, have not been entirely successful in providing consistent and smooth pressure regulation.

BRIEF SUMMARY

The background art does not provide smooth, consistent pressure regulation.

The present invention, in at least some embodiments, is an advance over the background art by providing cryosurgical systems and devices that exhibit smooth, constant pressure regulation and in which pressure is at least partially regulated through flow regulation.

An aspect of the present invention provides a system for selectively cooling and warming a tip of a cryosurgical instrument using a dual phase cryogen. The system includes: two sources of the cryogen, a first source storing the cryogen in a liquid phase and having a first source heater therein that selectively heats the liquid phase cryogen so as to convert at least some of the liquid phase cryogen stored therein into gaseous phase cryogen and a second source storing the cryogen in a gaseous phase; a first delivery path between the first source and the tip; a second delivery path between the second source and the tip; a cryogen delivery control section that selectively delivers cryogen to the tip from the respective sources; a cryogen return path from the tip to the first and second sources; a cryogen return control section that controls the return of cryogen via the cryogen return path and that includes a pump that pumps the returning cryogen to the second source; and a pressure control section including a first pressure sensor that senses a pressure in the first source, a second pressure sensor that senses a pressure in the second source, and a pressure regulator that regulates the pressure of the first source based on information from the pressure sensors.

Another aspect of the present invention provides an apparatus for delivering a phase changing cryogen to a surgical device, including: a first reservoir of the cryogen in a liquid phase; a liquid feed conduit through which cryogen travels from the first reservoir to the surgical device; a second reservoir of the cryogen in a gaseous phase; a gaseous feed conduit through which cryogen travels from the second reservoir to the surgical device; a return conduit through which cryogen that is exhausted from the surgical device returns to the first and/or second reservoir, the exhausted cryogen being in the gaseous phase; a pump disposed in the return conduit, the pump selectively pumping the returning cryogen to the first reservoir and/or the second reservoir; and a logic section that selectively energizes the pump to control an overall pressure in the system, based on information from pressure sensors and flow meters.

Still another aspect of the present invention provides a system including: a first cryogen delivery loop including a liquid cryogen storage section in fluid communication with a cryosurgical device via (i) a liquid cryogen delivery path and (ii) a cryogen return path; and a second cryogen delivery loop including a gaseous cryogen storage section in gaseous communication with (i) the cryosurgical device via a gaseous cryogen delivery path and a portion of the return path and (ii) the liquid cryogen storage section via a portion of the cryogen return path. The cryogen return path delivers exhausted, gaseous cryogen from the cryosurgical device to the first and/or the second cryogen storage section, includes a heater that selectively heats the exhausted, gaseous cryogen to maintain a temperature thereof above a boiling temperature of the cryogen, and includes a pump that selectively increases a local pressure in the cryogen return path. When the liquid cryogen heater is energized, liquid cryogen in the liquid cryogen storage section is converted into a gaseous state and delivered to the second cryogen storage section.

Yet another aspect of the present invention provides a system for selectively cooling and warming a tip of a cryosurgical instrument using a dual phase cryogen, including: two sources of the cryogen, a first source storing the cryogen in a liquid phase and having a first source heater therein that selectively heats the liquid phase cryogen so as to convert at least some of the liquid phase cryogen stored therein into gaseous phase cryogen and a second source storing the cryogen in a gaseous phase; a first delivery path between the first source and the tip; a second delivery path between the second source and the tip and including a gaseous phase cryogen heater that heats gaseous phase cryogen traveling therein from the second source to the tip; a cryogen delivery control section that selectively delivers cryogen to the tip from the respective sources; a cryogen return path from the tip to the first and second sources; a cryogen return control section that controls the return of cryogen via the cryogen return path and that includes a cryogen heater that selectively heats cryogen in the cryogen return path to maintain a temperature of returning cryogen therein above a boiling temperature thereof, a flow meter that measures a flow rate of the returning cryogen, and a pump that pumps the returning cryogen to the second source; and a pressure control section including a first pressure sensor that senses a pressure in the first source, a second pressure sensor that senses a pressure in the second source, and a pressure regulator that regulates an overall pressure of the system based on information from the pressure sensors and the flow meter.

Still another aspect of the present invention provides a system for selectively cooling and warming a tip of a cryosurgical instrument using a dual phase cryogen. The system includes: two sources of the cryogen, a first source storing the cryogen in a liquid phase and having a container contained completely within said first source, said container also containing the cryogen in a liquid phase, said container communicating fluidly with said first source through a check valve, wherein if pressure is greater in said first source than in said container, said check valve opens and cryogen in said liquid phase flows from said first source to said container; a second source storing the cryogen in a gaseous phase; a first delivery path between the first source and the tip; a second delivery path between the second source and the tip; a cryogen delivery control section that selectively delivers cryogen to the tip from the respective sources; a cryogen return path from the tip to the first and second sources; a cryogen return control section that controls the return of cryogen via the cryogen return path and that includes a pump that pumps the returning cryogen to the second source; and a pressure control section including a first pressure sensor that senses a pressure in the first source, a second pressure sensor that senses a pressure in the second source, and a pressure regulator that regulates an overall pressure of the system based on information from the pressure sensors.

As used herein, the term "cryoprobe" is provided as a non-limiting example of a cryosurgical instrument. And, although embodiments and/or aspects of the present invention are discussed in the context of a cryoprobe, it is to be understood that other cryosurgical instruments are both contemplated and intended to be included.

Without wishing to be limited in any way, and without wishing to provide a closed list, the present invention in at least some embodiments effectively regulates "two-phase flow", in which the cryogen both flows and boils, thereby controlling the level of the heat flux.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which.

DETAILED DESCRIPTION

Figure 1:
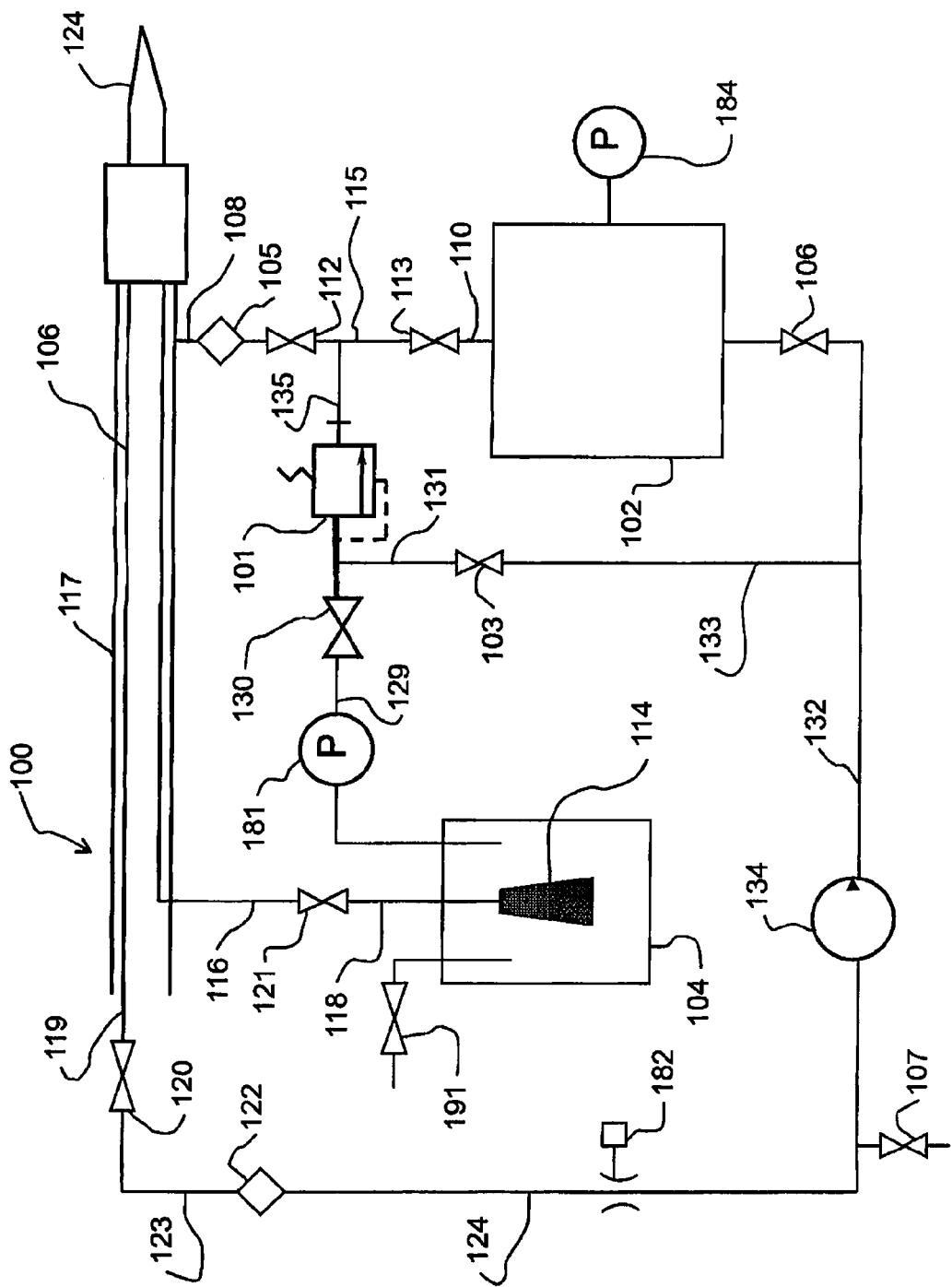
FIG. 1 shows a closed loop system 100 consistent with an embodiment of the present invention.

Reference will now be made in detail to embodiments of the present invention, examples of which are illustrated in the accompanying drawings, wherein like reference numerals refer to the like elements throughout. The embodiments are described below to explain the present invention by referring to the figures. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining exemplary embodiments of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to FIG. 1, there is illustrated a closed loop system 100 for recycling a gaseous cryogen in a pressurized manner, while the pressure and the flow in the system are regulated. The system 100 includes a source of liquid cryogen 104, a source of gaseous cryogen 102, a cryoprobe 117, and structures providing various cryogen flow paths, which are discussed in detail below.

The source of liquid cryogen 104 is connected to the cryoprobe 117 via, in series from upstream to downstream, a line 118, a two-way valve, 121, and a cryoprobe inlet 116.

The source of gaseous cryogen 102 is connected to the cryoprobe 117 via, in series from upstream to downstream, a line 110, a two-way valve 113, a line 115, a two-way valve 112, a heater 105, and a cryoprobe inlet 108.

The cryoprobe 117 is connected to the gaseous cryogen source 102 via, in series from upstream to downstream, a line 119, a two-way valve 120, a line 123, a heater 122, a line 124, a pump 134, a line 132, and a two-way valve 106. A flow meter 182 and a relief valve 107 may be connected to line 124 between the heater 122 and the pump 134.

The cryoprobe 117 is connected to the liquid cryogen source 104 via, in series, a line 133 that is connected to line 132 at a point between the pump 134 and the two-way valve 106, two-way valves 103 and 130, a line 129, and a pressure indicator 181.

Also present in the system 100 is a pressure regulator connected to a line 135 that interconnects the two-way valve 130 and the line 115.

A cryoablation procedure may include one or more alternating cooling and active thawing processes, which follow an initialization procedure.

Operation of the system 100 is discussed. During a freezing process of the cryoablation procedure, liquid cryogen exits from source 104 through the line 118. Flow is controlled by either the pressure regulator 101, or by the two-way valve 121, although during the freezing process the two-way valve 121 is typically in the open state. The flow of the liquid cryogen is controlled as the liquid cryogen boils, thereby limiting the heat flux to assure smooth operation, as previously described. Cryogen then enters through the inlet 116 and into the cryoprobe 117 where it then cools a tip 124, which may optionally be solid or hollow. Exhausted cryogen (i.e., cryogen that has cooled the surrounding environment through boiling and has expanded, as the liquid portion of the cryogen is reduced relative to the gaseous portion) then exits through a return tube 106 of the cryoprobe 117 to the line 119. The exhausted cryogen then passes through the two-way valve 120 and is optionally heated by the heater 122 to ensure that the return line temperature is above the boiling temperature of the cryogen, such that the exhausted cryogen is maintained in a gaseous state. Optionally and alternatively, the cryogen is not heated. The gaseous cryogen then flows through a line 124 and a flow meter 182, which measures the rate of flow of cryogen through the line 124. As described in greater detail below, this flow rate information is one component upon which the pressure regulation for system 100 is based. Optionally, if the flow rate is too high for the desired pressure in system 100 to be maintained and/or for effectively cooling tip 124, gaseous cryogen may be exhausted through a relief valve 107.

The gaseous cryogen, if not exhausted, then passes to the pump 134, which is controlled to maintain the desired pressure in system 100. Pump 134 pumps the gaseous cryogen to gaseous cryogen source 102 through the line 132 and then through the two way valve 106. The desired gaseous state of the cryogen upon entering pump 134 is maintained by the heater 122, as previously described. Optionally, the gaseous cryogen may be pumped through the two-way valve 103 to the line 131 and hence through the two way valve 130 to the liquid cryogen source 104 through the line 129. This optional flow path may be advantageous in maintaining the desired pressure differential between the liquid cryogen source 104 and the gaseous cryogen source 102 as described in greater detail below.

System pressure is measured at liquid cryogen source 104 by the pressure gauge 181 and at the gaseous cryogen source 102 by the pressure gauge 184. Preferably, pressure is higher at the source of gaseous cryogen 102 than at the source of liquid cryogen 104.

The pressure regulator 101 and the pump 134 control the overall pressure of system 100. In more detail, pressure regulator 101 receives information regarding the pressure of system 100 from pressure gauge 181 and flow meter 182 and, based on this received information, the activity of pump 134 may be adjusted through a suitable electronic circuit (not shown) such that the pressure in the gaseous cryogen source 102 is preferably maintained at a higher level than the pressure in the liquid cryogen source 104. Optionally, in case of excessive systemic pressure, cryogen gas may be exhausted through valve 107. Also, optionally, in case of excessive pressure at liquid cryogen source 104, gaseous cryogen may be exhausted through the relief valve 191. Preferably however, gaseous cryogen is recycled to gaseous cryogen source 102 and the desired pressure is maintained in system 100.

During the active thawing process, the gaseous cryogen flows from gaseous cryogen source 102 through the line 110, the two-way valve 113, the line 115, the two-way valve 112 and is heated by the heater 105, after which the heated gaseous cryogen enters the cryoprobe 117 through the inlet 108. This gaseous cryogen continues to flow through the line 119 to the pump 134. Pump 134 raises the pressure of the gaseous cryogen and returns the gaseous cryogen to the gaseous cryogen source 102. During this operation valve 107 remains closed and the gaseous cryogen is fully recycled.

During an initialization process of the system, when the flow meter 182 indicates that cryogen is not flowing, the pump 134 is first pumping either air or cryogen into source 104, by opening valves 103 and 130 for line 129, and also by opening valve 107 to permit entry of air. When the pressure indicator 181 reaches a determined (threshold) value, valve 103 closes and valve 106 opens to deliver the compressed gas to the source 102, until the pressure at source 102 reaches another determined value, as read by pressure sensor 184.

During the freezing phase of operation, when valves 121 and 120 are open and flow meter 182 indicates flow is occurring, pump 134 is primarily activated to return cryogen to the source 102 through the valve 106, as long as the pressure as measured by pressure meter 181 is maintained at the desired value or range of values. If the pressure meter 181 indicates that the pressure is below the desired value threshold, then pump 134 forces the cryogen through valves 103 and 130 into the source 104. During the active thawing phase of operation, pump 134 simply recycles the cryogen through valves 106, 113, 112 and 120 through lines 110, 108 and 119.

Figure 2:
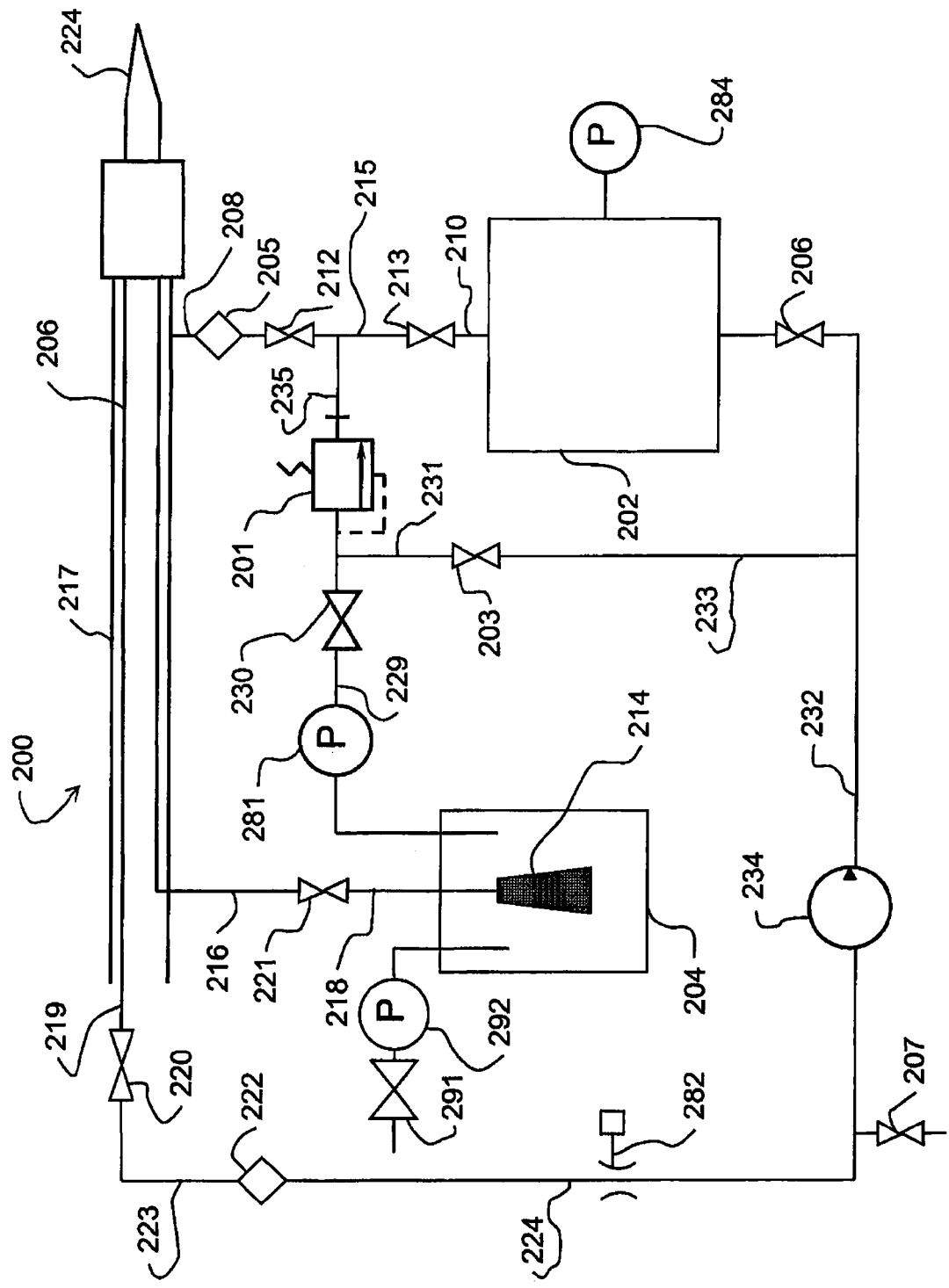
FIG. 2 shows a closed loop system 200 consistent with an embodiment of the present invention featuring a constantly operating pump.

Referring now to FIG. 2, there is illustrated a system 200 consistent with an embodiment of the present invention. The system 200, in some respects, operates similarly to system 100 of FIG. 1. Thus, for ease of explanation, like components between systems 100 and 200 share corresponding reference numbers and detailed description thereof is omitted.

A feature of the system 200 that differentiates it from the system 100 is that pump 234 operates constantly to recycle the cryogen return gas. Furthermore, the pump 234 is preferably able to pump both liquid cryogen and gaseous cryogen. In order to maintain pressure in system 200, rather than controlling the activity of pump 234, the pressure regulator 201 preferably controls the exhaust of excess gaseous cryogen through a relief valve 291 at liquid cryogen source 204. Pressure gauge 292 is preferably located between liquid cryogen source 204 and relief valve 291, to determine the pressure at liquid cryogen source 204. In system 200, where the pump 234 can handle liquid as well as gaseous cryogen, the operation of heater 222 is reserved only for cases when the gaseous cryogen is exhausted through relief valve 207.

Figure 3:
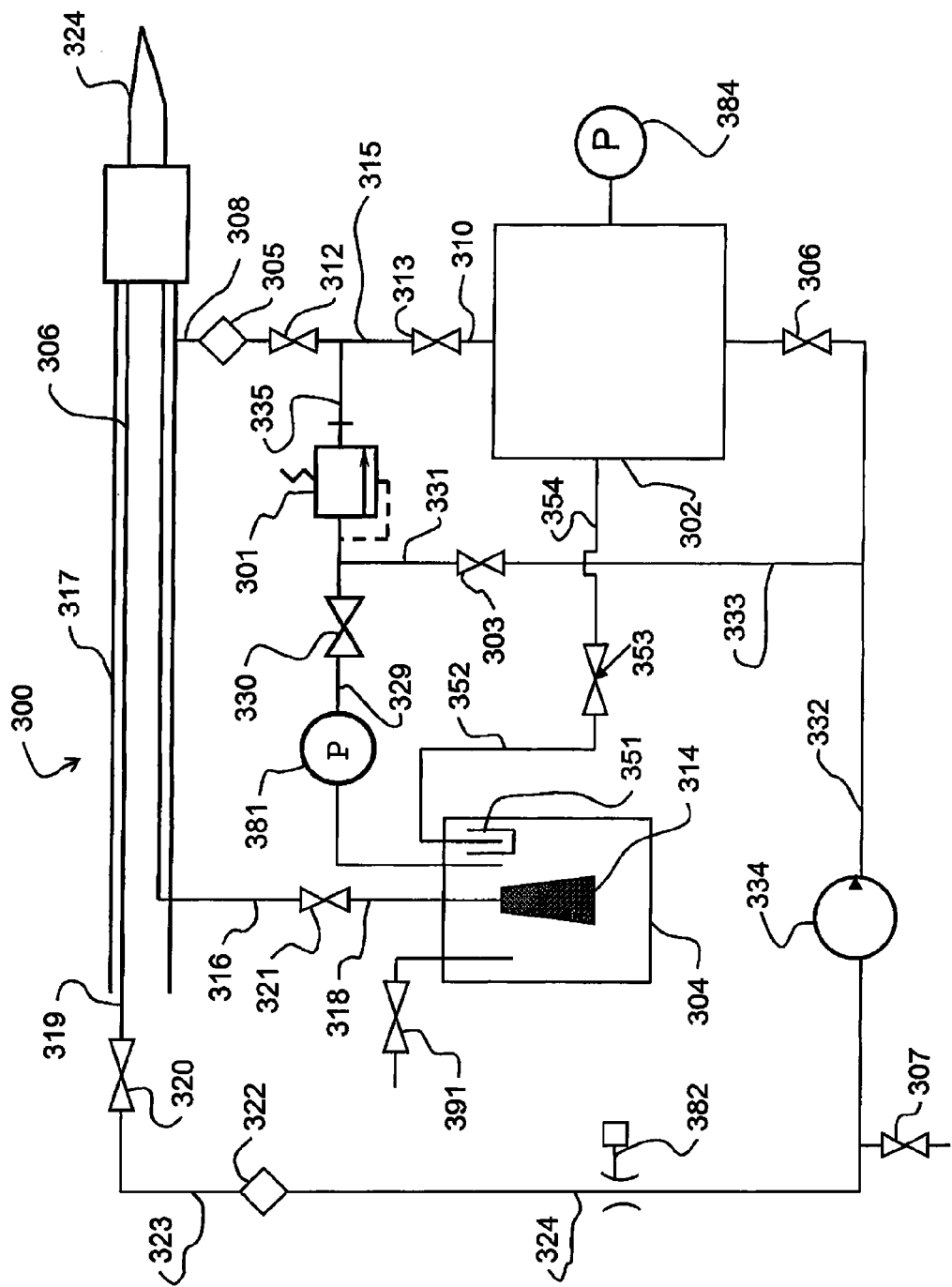
FIG. 3 shows a closed loop system 300 consistent with an embodiment of the present invention featuring an additional structure to generate gaseous cryogen.

Referring now to FIG. 3, there is illustrated a system 300 consistent with an embodiment of the present invention. The system 300, in some respects, operates similarly to system 100 of FIG. 1. Thus, for ease of explanation, like components between systems 100 and 300 share corresponding reference numbers and detailed description thereof is omitted.

A feature of the system 300 that differentiates it from the system 100 is the presence of additional structure to generate gaseous cryogen in order to fill gaseous cryogen source 302. In more detail, the sources of cryogen 302 and 304 are connected by line 352, a two-way valve 353, and a line 354, in series from the source 304 to the source 302. Also present is a heater 351 disposed in the source 304.

In operation, the additional structure generates gaseous cryogen by energizing heater 351 to heat and boil liquid cryogen in the liquid cryogen source 304. The gaseous cryogen at liquid cryogen source 304 is then preferably directly transferred to gaseous cryogen source 302 through a line 352 and a two-way valve 353, thereby rapidly increasing the pressure at gaseous cryogen source 302 to the desired pressure and more rapidly enabling system 300 to achieve the desired system pressure. The additional structure is preferably operative during the initiation of the activity of system 300 (i.e., upon initiation of cryotherapy).

Figure 4:
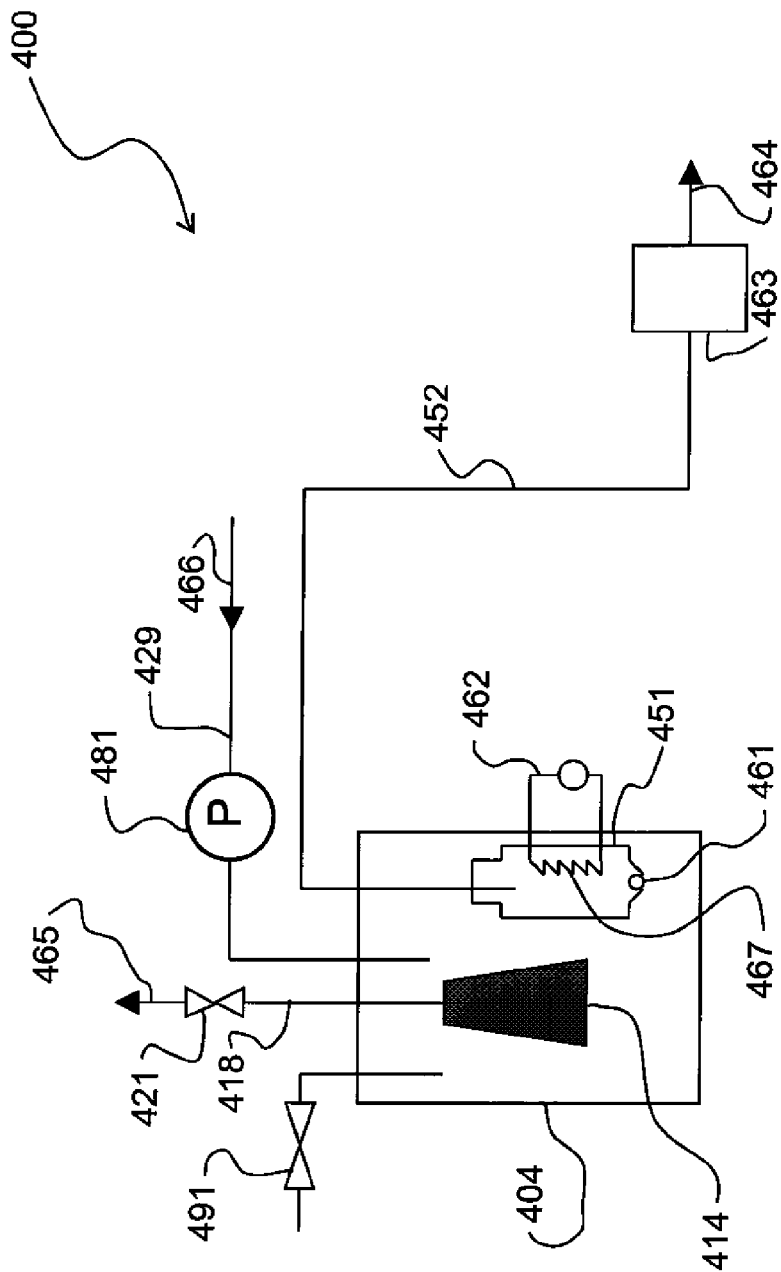
FIG. 4 shows a partial view of a closed loop system 400 consistent with an embodiment of the present invention featuring additional pressure control structure.

Referring now to FIG. 4, there is illustrated a portion system 400 consistent with an embodiment of the present invention. The system 400, in some respects, operates similarly to system 100 of FIG. 3. Thus, for ease of explanation, like components between systems 100 and 400 share corresponding reference numbers and detailed description thereof is omitted.

A feature of the system 400 that differentiates it from the system 100 is additional structure for controlling pressure. In more detail, the pressure control structure includes a closed container 451, a line 452 extending from one end of the closed container, and a check valve 461 at another end of the closed container. A heater 467 is disposed in the closed container 451 and is controlled by a control circuit 462.

In system 400, the first source 404 contains liquid cryogen. Inside of the first source 404 there is an additional closed container 453. The container 451 permits cryogen to flow in through a check valve 461 when the pressure in first source 404 is greater than the pressure in container 453. When an electrical heater 467 is activated, the pressure in the container 451 is raised and the check valve 461 is closed. As the pressure increases with the boiling that occurs due to the heating, gaseous cryogen flows in the direction 464 which connects container 451 with the second source of gaseous cryogen (not shown), at a pressure set by pressure regulator 463. During the freezing or cooling mode of operation, liquid cryogen flows through a filter 414, when valve 421 is open to a cryoprobe (cryosurgical device, not shown) in the direction indicated by the arrow 465. When the pressure in the first source 404 is lower than desired, pressured gaseous cryogen enters through a line 429, upstream of which is an additional pressure regulator of in the direction indicated by 466.

During the initialization of the system 400, the electrical heater 467 is activated and boils the cryogen in container 451. When the pressure reaches a determined value, the pressure regulator 463 opens and the compressed gaseous cryogen is transferred in the direction 464 to the second source (not shown). During other phases of operation the system 400 operates in a manner at least similar to system 100.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

The various described embodiments may be selectively combined.

Although selected embodiments of the present invention have been shown and described, it is to be understood the present invention is not limited to the described embodiments. Instead, it is to be appreciated that changes may be made to these embodiments without departing from the principles and spirit of the invention, the scope of which is defined by the claims and the equivalents thereof.

What is claimed is:

1. A system for delivering a phase changing cryogen to a surgical device, comprising:
    a first reservoir of the cryogen in a liquid phase;
    a liquid feed conduit through which cryogen travels from the first reservoir to the surgical device;
    a second reservoir of the cryogen in a gaseous phase;
    a gaseous feed conduit through which cryogen travels from the second reservoir to the surgical device;
    a return conduit through which cryogen that is exhausted from the surgical device returns to at least one of the first and second reservoir, the exhausted cryogen being in the gaseous phase;
    a cryogen return control section that controls the return of cryogen via the return conduit and that includes a pump disposed therein, the pump selectively pumping the returning cryogen to at least one of the first and second reservoir;
    a pressure control section including a first pressure sensor that senses a pressure in the first reservoir, a second pressure sensor that senses a pressure in the second reservoir, and a pressure regulator that regulates the pressure of the first reservoir based on information from the pressure sensors, wherein said pressure regulator is placed between said first and second reservoirs; and
    a logic section that selectively energizes the pump to control an overall pressure in the system, based on information from the pressure sensors and flow meters.

2. The system of claim 1, further comprising an exhaust section that exhausts cryogen gas from the return conduit, when a pressure in the first reservoir exceeds a specified threshold.

3. The system of claim 2, wherein, when the exhaust section is closed, the gaseous cryogen from the cryosurgical device is fully recycled from a tip thereof back to the either one or both of the reservoirs.

4. The system of claim 1, wherein the pressure regulator regulates an overall pressure of the system by regulating pressure in the first reservoir.

5. The system of claim 1, further comprising cryogen delivery control section that comprises one or more two-way valves disposed in one or more of the conduits.

6. The system of claim 1, further comprising: a heater disposed in the return conduit, the heater selectively heating the returning cryogen so that it remains in the gaseous phase.

7. The system of claim 6, wherein the apparatus cools a tip of the surgical device by delivering liquid phase cryogen to the tip via the liquid feed conduit, and wherein the system warms the tip by delivering gaseous phase cryogen from the second reservoir to the tip via the gaseous feed conduit, the delivered gaseous phase cryogen being warmed by the heater.

8. The system of claim 6, wherein said logic section also controls said heater.

* * * * *